US007426256B2

(12) United States Patent
Rasche et al.

(10) Patent No.: US 7,426,256 B2
(45) Date of Patent: Sep. 16, 2008

(54) MOTION-CORRECTED THREE-DIMENSIONAL VOLUME IMAGING METHOD

(75) Inventors: Volker Rasche, Hamburg (DE); Babak Movassaghi, Hamburg (DE); Marcel Boosten, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 20 days.

(21) Appl. No.: 10/549,267

(22) PCT Filed: Mar. 12, 2004

(86) PCT No.: PCT/IB2004/050239

§ 371 (c)(1),
(2), (4) Date: Sep. 13, 2005

(87) PCT Pub. No.: WO2004/081877

PCT Pub. Date: Sep. 23, 2004

(65) Prior Publication Data
US 2006/0210019 A1 Sep. 21, 2006

(30) Foreign Application Priority Data
Mar. 14, 2003 (EP) ................... 03100646

(51) Int. Cl.
*A61B 6/03* (2006.01)
(52) U.S. Cl. ....................................... 378/8
(58) Field of Classification Search ..................... 378/4, 378/8, 901; 382/128, 131; 600/410, 413, 600/5; 708/813
See application file for complete search history.

(56) References Cited

U.S. PATENT DOCUMENTS

| 4,961,426 A | 10/1990 | Spraggins |
| 6,198,959 B1 | 3/2001 | Wang |
| 6,501,848 B1 * | 12/2002 | Carroll et al. ............... 382/128 |
| 7,113,623 B2 * | 9/2006 | Chen et al. .................. 382/128 |
| 2002/0118866 A1 | 8/2002 | Breeuwer et al. |
| 2002/0126794 A1 * | 9/2002 | Rasche et al. ................. 378/8 |

(Continued)

FOREIGN PATENT DOCUMENTS

DE WO 0103639 * 12/2002

(Continued)

OTHER PUBLICATIONS

Koenig, A., et al.; Dynamic Reconstruction for Radiotherapy Planning; 2002; CARS;pp. 521-526.*

(Continued)

*Primary Examiner*—Chih-Cheng Kao
*Assistant Examiner*—John M Corbett

(57) ABSTRACT

An X-ray imaging method forms a set of a plurality of two-dimensional X-Ray projection images of a medical or veterinary object to be examined through a scanning rotation by an X-Ray source viz à viz the object. Such X-Ray images are acquired at respective predetermined time instants with respect to a functionality process produced by the object. From said set of X-Ray projection images by back-projection a three-dimensional volume image of the object is reconstructed. In particular, an appropriate motion correction is derived for the respective two-dimensional images, and subsequently as based on a motion vector field from the various corrected two-dimensional images the intended three-dimensional volume is reconstructed.

17 Claims, 2 Drawing Sheets

U.S. PATENT DOCUMENTS

| | | | |
|---|---|---|---|
| 2002/0131650 A1* | 9/2002 | Rodet et al. | 382/280 |
| 2002/0136438 A1 | 9/2002 | Breeuwer | |
| 2003/0007593 A1* | 1/2003 | Heuscher et al. | 378/4 |
| 2004/0136490 A1* | 7/2004 | Edic et al. | 378/4 |

FOREIGN PATENT DOCUMENTS

| | | |
|---|---|---|
| EP | 1 087 339 A1 | 3/2001 |
| WO | WO 01/43642 A2 | 6/2001 |
| WO | WO 02/36011 A1 | 5/2002 |
| WO | WO 02/103639 A2 | 12/2002 |
| WO | WO 03/045263 A2 | 6/2003 |

OTHER PUBLICATIONS

Kehl et al.; Computers & Graphics 24 (2000) 731-739.*
Bookstein, Principal Warps: Thin-Plate Splines and the Decomposition of Deformations, Jun. 6, 1989, IEEE Transactions on Pattern Analysis and Machine Intelligence, vol. 11, No. 6, pp. 567-585.*
Dougherty, L., et al.; Validation of an Optical Flow Method for Tag Displacement Estimation; 1999; IEEE; p. 1.
Kehl, H.G., et al.; 3D Heart Modelling from Biplane, Rotational Angiocardiographic X-Ray Sequences; 2000; Computers & Graphics; 24:731-739.
Koenig, A., et al.; Dynamic Reconstruction for Radiotherapy Planning; 2002; CARS; pp. 521-526.

* cited by examiner

MOTION-CORRECTED THREE-DIMENSIONAL VOLUME IMAGING METHOD

BACKGROUND OF THE INVENTION

The invention relates to an X-ray imaging method, comprising the forming of a set of a plurality of two-dimensional X-Ray projection images of a medical or veterinary object to be examined through a scanning rotation by an X-Ray source viz à viz said object, which X-Ray images are acquired at respective predetermined time instants with respect to a functionality process produced by said object, and from said set of X-Ray projection images reconstructing by back-projection a three-dimensional volume image of said object.

Such methods have been in use for cardiac and other medical diagnostic operations. The prime problem for acquiring an appropriate 3D or 4D data set from the 2-dimensional images is the movement of items within the human or other body under consideration, which movement is sometimes substantially periodic, but not completely so. In other circumstances, the object in question, such as an intestine can be considered as moving in quite an irregular manner. Furthermore, the object may undergo secondary motion, such as caused by breathing or consciously moving. It is therefore a problem that various two-dimensional images do not refer back to an identical 3D object, which would render their applicability less good. However, for a top-quality reconstruction the number of processed two-dimensional images should be as high as possible, whilst raising the amount of available data that is in the same "phase" of the motion, as far as such phase is detectable.

SUMMARY TO THE INVENTION

In consequence, amongst other things, it is an object of the present invention to raise the number of useful two-dimensional images by providing motion correction for the respective two-dimensional images to reconstruct from various corrected two-dimensional images the intended three-dimensional volume. As disclosed hereinafter in additional detail, the correction may be based on feature extraction and/or three-dimensional feature matching, such as through markers, bifurcations, or other.

Now therefore, according to one of its aspects, the invention relates to an X-ray imaging method comprising the steps of forming a set of a plurality of two-dimensional X-Ray projection images of a medical or veterinary object to be examined through a scanning rotation by an X-Ray source viz à viz said object, which X-Ray images are acquired at respective predetermined time instants with respect to a functionality process produced by said object; reconstructing by back-projection a three-dimensional volume image of said object from the set of X-Ray projection images, and deriving an appropriate motion correction for the respective two-dimensional images as based on a motion vector field, and subsequently from the various corrected two-dimensional images reconstructing the intended three-dimensional volume.

The invention also relates to a three-dimensional X-Ray apparatus being arranged for implementing a method comprising the steps of forming a set of a plurality of two-dimensional X-Ray projection images of a medical or veterinary object to be examined through a scanning rotation by an X-Ray source viz à viz said object, which X-Ray images are acquired at respective predetermined time instants with respect to a functionality process produced by said object; reconstructing by back-projection a three-dimensional volume image of said object from the set of X-Ray projection images, and deriving an appropriate motion correction for the respective two-dimensional images as based on a motion vector field, and subsequently from the various corrected two-dimensional images reconstructing the intended three-dimensional volume. Further advantageous aspects of the invention are recited in dependent claims.

BRIEF DESCRIPTION OF THE DRAWING

These and further features, aspects and advantages of the invention will be discussed more in detail hereinafter with reference to the disclosure of preferred embodiments of the invention, and in particular with reference to the appended Figures that illustrate.

DETAILED DESCRIPTION OF PREFERRED EMBODIMENTS

Figure 1:
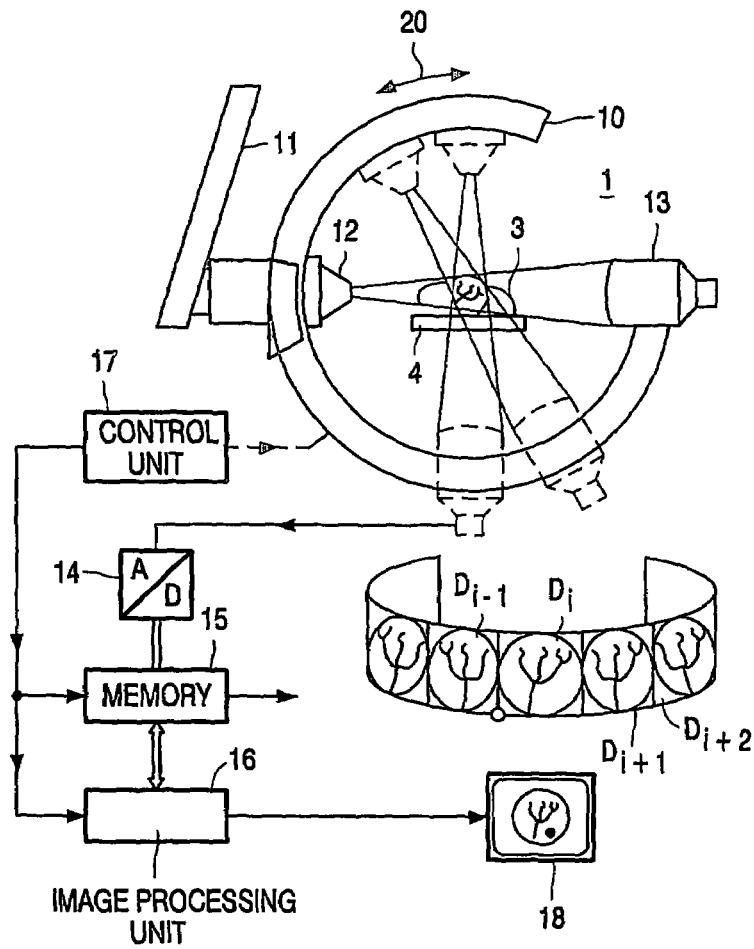
FIG. 1, an X-Ray imaging apparatus, in which the invention may be applied.

FIG. 1 illustrates an exemplary X-Ray imaging apparatus in which the invention may be applied. Basically, the apparatus allows to form two-dimensional X-Ray images of an object to be examined, in particular an object that moves (quasi-)periodically, such as a heart and its associated coronary vascular system, or alternatively, an object that moves rather unpredictably, such as an intestine or part thereof. From the combining of various such two-dimensional images, a three-dimensional volume of the object should be obtained. By itself, such three-dimensional reconstruction is state of the art. Similar technology may be used to produce a four-dimensional data set such as representing a selected part of the heart during a phase interval of its motion.

Now, the imaging apparatus 1 includes a C-arm 10 that is mounted on a partially shown stand 11. The C-arm can be rotated over an angle such as 180° around its center in the direction of double arrow a 20 through a motor drive not shown. The C-arm accommodates an X-Ray source 12 and an X-Ray image pick-up 13, that are aligned relative to each other in such a manner that an X-Ray image can be formed of a certain volume around the above center. This plurality of X-Ray images show the volume under examination generated by respective different angular orientations of the image forming system 12, 13, that are in part shown by dashed lines. The pick-up device may be a series arrangement of an X-Ray image intensifier that feeds a television chain, while the signals furthermore are A/D converted (14) and stored (15), so that the complete examination yields a series of images ( . . . $D_{i-1}, D_i, D_{i+1}, D_{i+2}$ . . . ). These X-Ray images can themselves be processed by known reconstruction methods (16) to obtain a three-dimensional volume for examination. This volume or various projections therethrough can be displayed on monitor 18. The various subsystems of the imaging apparatus are controlled by controller 17. Another applicable apparatus could be based on multi-slice CT-scanning.

Figure 2:
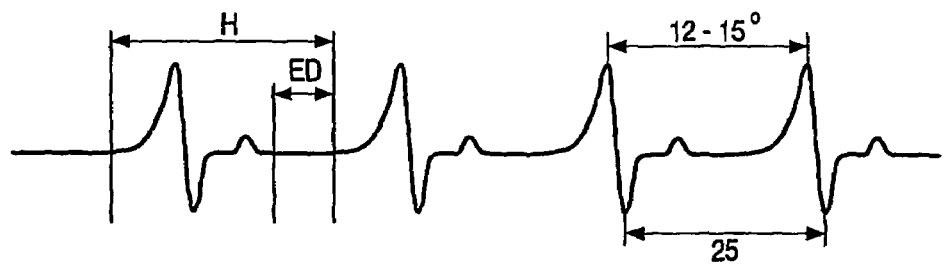
FIG. 2, a cardiac cycle and various applicable data acquisition instants therein.

FIG. 2 illustrates a cardiac cycle and various applicable data acquisition instants therein. For simplicity, the cardiac cycle H has been shown as ideally periodic; in practice, large variations may occur. Preferred data acquisition instants for a three-dimensional image are located during end diastole ED on an ECG scale; during this period, the heart geometry is relatively stationary. The scanning speed of the arm may be 180° in some 15 to 20 seconds, at a standard heartbeat rate of some 60 beats per minute, and delivering 25 images per second. This would imply an angle variation of some 12-15 degrees and a number of images of some 25 for one heartbeat, as has been indicated in the idealized Figure. The motion of an intestine or artery would likewise occur on time scales ranging from fractions of a second to several seconds.

Now, a cardiologist may position a stent delivery catheter provided with markers into a region of interest (ROI). By themselves, such markers have been in wide use to facilitate interpreting X-Ray images. The markers may show on the X-Ray images as relatively darker, or relatively lighter dots with respect to the contrast fluid. Alternatively, no contrast fluid is used, and the observable contrast is relative to the blood. Next, after positioning the center of rotation near the ROI, by moving either the patient or the apparatus, a rotational scan of the cardiac ROI is made. Note that the usage of so-called guide wires provided with multiple markers allows to use a larger ROI, or rather, to improve the quality of the resulting image.

Fundamental in this embodiment is the compensating for cardiac or other movement by correcting the two-dimensional images of the rotational scan prior to the back-projection. By itself, movement compensation technique has been disclosed in documents EP 02 292 995.4, EP 03 290 455.9, and EP 02 292 336.1 assigned to the present assignee. Such technique allows (1) identifying the markers/features in the two-dimensional image; (2) motion correction through two-dimensional image-warping through a motion vector field, such that identified markers/features are moved to their two-dimensional reference position, while using interpolation to correct the rest of the image. Essential is the determination of the two-dimensional reference positions for each image to which the markers/features identified in that image are to be corrected to. To determine the two-dimensional reference position of each marker/feature in each image, the following steps are executed:

ECG-based Reference Image selection: the ECG signal is used to select two reference images that are in the same cardiac cycle phase and under an appreciable angular distance. Such angular distance may range between about 90° and for example 45°. Preferably, a relatively large rotary angle should be used effectively. Cardiac phase determination via ECG signal analysis has been state of the art for both Cardiac Modelling and for Cardiac Reconstruction. Reference images with approximately 90° are used in Cardiac Modelling. Other techniques for such selection are likewise applicable.

Reference marker/feature Identification in 3D. The markers/features are identified on one of the reference images. This identification may need only two markers/features selected by a user person, and may even be fully automated. Using the epipolar projection line of the markers/features, these are automatically identified in any other reference image. Thereby, the three-dimensional positions of the markers/features will be known.

Projection of three-dimensional reference markers/features to 2D. For each of the two-dimensional images of the rotational scan, the two-dimensional position of the reference markers/features is determined by projecting the position of the three-dimensional marker/feature onto the image. For each image, this determines the two-dimensional reference positions to which the markers/features found in that image will be corrected.

Correction-Based Projection Image Selection

The "amount of movement correction" can be measured by for example the distance between the identified two-dimensional marker position and the reference two-dimensional marker position, or through an ECG analysis, or by a combination of the two methods. By selecting images for which the amount of movement correction is less than a certain value, the image quality aspects of the reconstruction can be influenced: a trade-off in the number of images used for reconstruction versus the similarity between images can be made. By balancing this value, the image quality of cardiac reconstructions can be influenced, and therefore, optimized for its intended (clinical) purpose.

Threedimensional Reconstruction

Via the state of the art Feldkamp Back-Projection Reconstruction, a three-dimensional volume is created based on the selected projection images. The volume is then visualized for clinical analysis. The image quality of the resulting three-dimensional reconstruction is expected to be clinically usable near the markers/features, and therefore, in the ROI.

Overlay of Multiple Threedimensional Reconstructions

Since "cardiac motion compensation" is built into three-dimensional Cardiac ROI reconstruction, multiple runs of the cardiac region may be made and overlaid adequately. This requires the markers to be left at the same position in the patient, while making the multiple Cardiac ROI Reconstructions. This allows for example a coronary artery, a placed stent, and also a plaque within the ROI to be visualized in a single three-dimensional view.

Further Aspects of the Invention

Now in the above, a prime difficulty is the correct determination of the gating window for deriving a projection of the moving object. Although in principle such gating window may be derived from analysing an ECG signal simultaneously with taking the measurements, the present inventors have concluded that the analysis for determining the gating instants should better be based on analysing the data proper. An advantageous embodiment therefore is following one or more feature points, such as arterial bifurcation points or bone elements, which would be quite feasible over a heart cycle. Such would then essentially imply a four-dimensional motion tracking of the coronary feature points, which will be more in detail discussed hereinafter. The temporally resolved three-dimensional locations of the feature points over the cardiac cycle can be used for velocity and acceleration analysis of the coronaries, which would yield optimally suited feature-point-dependent temporal gating windows.

One of the particular problems with image reconstruction in a heart environment is the limited number of projections that are available for such reconstruction, which scarcity will often cause severe streaking artifacts in the final reconstructed image. Therefore, the number of usable projections should be substantially increased. This object is favourably effected by producing a two-dimensional motion compensation for those projections that by themselves have not been acquired in the most advantageous cardiac phase so that they would be transformed to represent their shape in such most advantageous phase. The embodiment approach in particular separates the motion of coronaries into two main components:

a non-linear component caused by the contraction of the heart;

a linear component caused by the rotation of the object.

Figure 3:
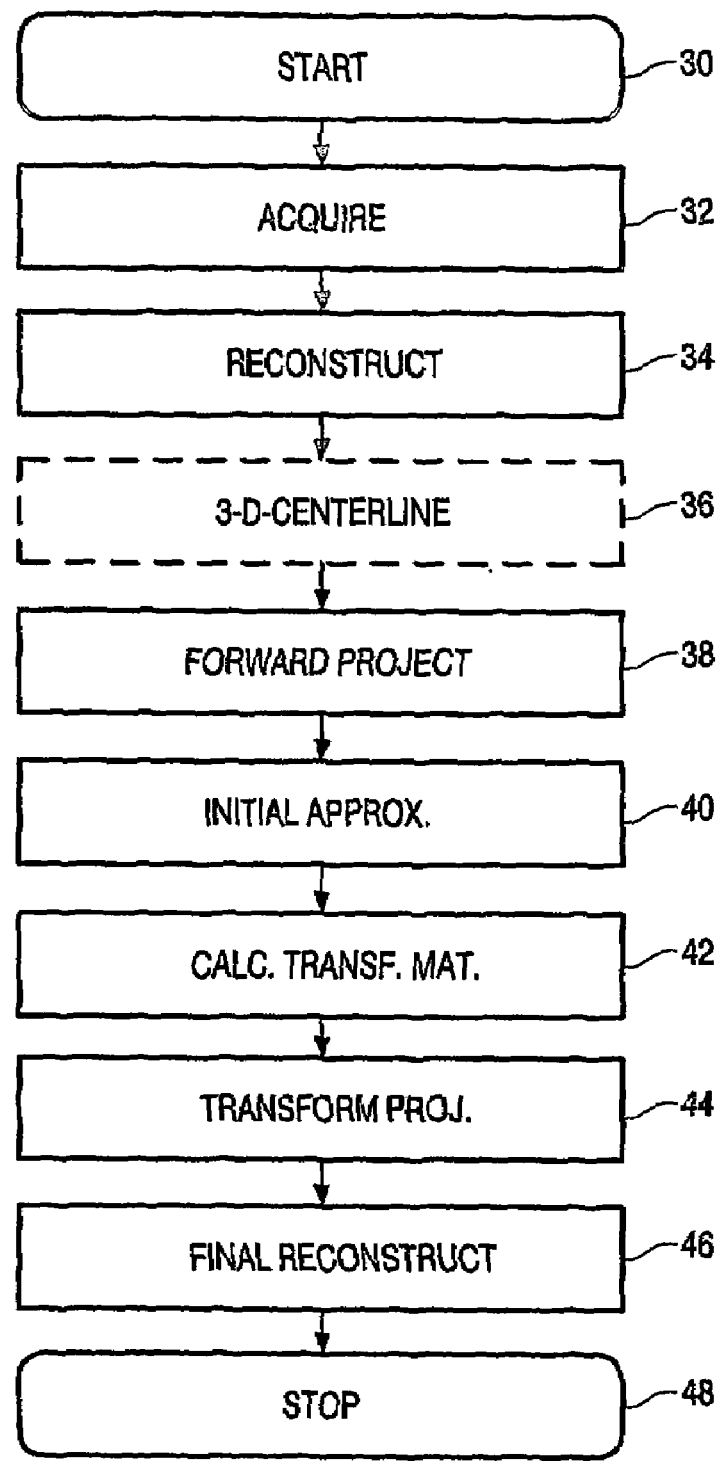
FIG. 3, a flow chart of a method embodiment.

The result is a transformation matrix that transforms the projection from one cardiac phase into another. Now, the motion-compensated two-dimensional projections are obtained as follows, whilst referring to FIG. 3 that illustrates a flow chart of the method. Now first, in block 30, the necessary hardware and software facilities are assigned. Then subsequently:

Acquiring a rotational angiography data set from a calibrated system (block 32);

Reconstructing a low-spatial-resolution volume data set for a specific heart phase (block 34);

(optional) Estimating a three-dimensional centerline in the volume data (block 36);

Forward projecting the volume data (or rather, the three-dimensional centerline) into the successively acquired projections with different projection geometry (block 38);

Using the forward projected volume, or rather, the centerline (cf #3) as an initial approximation for the correct motion-compensated projection for this viewing angle (block 40);

Calculating a transformation matrix between the initial approximation and the real acquired projection at the current viewing angle (block 42);

Transforming the acquired projection into the correct cardiac phase (block 44);

Incorporating the additionally acquired projections in the three-dimensional reconstruction procedure by the successive application of the above method on any or all appropriate projections (block 46). Subsequently, the process is stopped, or another series of measurements is undertaken (block 48).

Now, the present invention has hereabove been disclosed with reference to preferred embodiments thereof. Persons skilled in the art will recognize that numerous modifications and changes may be made thereto without exceeding the scope of the appended Claims. In consequence, the embodiments should be considered as being illustrative, and no restriction should be construed from those embodiments, other than as have been recited in the Claims.

The invention claimed is:

1. An X-ray imaging method comprising the following steps:
   forming a set of a plurality of two-dimensional X-Ray projection images of a medical or veterinary object to be examined through a scanning rotation by an X-Ray source and two-dimensional detector, which X-Ray images are acquired at respective predetermined time instants with respect to a functionality process produced by said object;
   separating an estimated motion of parts of said object into a non-linear temporal component caused by overall contraction within said object, and a linear temporal component caused by overall rotation within said object;
   reconstructing by back-projection a motion artifacted three-dimensional volume image of said object from the set of two-dimensional X-Ray projection images;
   deriving a motion correction for the respective two-dimensional images as based on a motion vector field;
   applying the motion correction to the set of two-dimensional X-ray projection images, generating a set of corrected two-dimensional X-ray projection images;
   from the set of corrected two-dimensional X-ray projection images, reconstructing a motion corrected three-dimensional volume;
   wherein said motion correction is derived from reference images that are acquired in corresponding instants of the movement of the object in question that is substantially periodic, and which reference images have substantially differing projection orientations.

2. The method as claimed in claim 1, wherein said corresponding instants of the movement include corresponding phases of a cardiac movement.

3. The method as claimed in claim 2, wherein said movement is derived from following one or more feature points of the object.

4. The method as claimed in claim 1, further including:
   deriving said motion vector field base on feature extraction.

5. The method as claimed in claim 1, wherein two-dimensional projections are corrected towards a calculated shape by the functionality process of said object.

6. The method as claimed in claim 1, applied to coronary arteries.

7. The method as claimed in claim 1, wherein said projection orientations differ by an angle in a range between substantially 45 degrees and 90 degrees.

8. The method as claimed in claim 1, wherein the object includes a coronary artery with a stent in place and an artery wall section of said artery.

9. The method as claimed in claim 1, further comprising deriving said motion correction from physical elements present in the object.

10. The method as claimed in claim 1, wherein said correction includes translation of said object.

11. The method as claimed in claim 1, further comprising deriving an amount of movement correction from a measured distance between an identified two-dimensional marker/feature position and a reference two-dimensional marker/feature position, or through an EGG analysis.

12. The method as claimed in claim 1, further comprising:
    generating and overlaying multiple projection images of a cardiac region whilst maintaining one or more markers at the same position, and making the multiple cardiac ROI reconstructions by overlaying the projection images.

13. The method as claimed in claim 1, further comprising generating a four-dimensional data set.

14. The method as claimed in claim 1, further comprising:
    determining temporal gating based on three-dimensionally resolving a feature point location.

15. The method as set forth in claim 1, further including:
    creating a transformation matrix that transforms the three-dimensional volume image from one phase into another.

16. A method comprising:
    Acquiring a rotational angiography data set including a plurality of projections at each of a plurality of viewing angles;
    Reconstructing a low-spatial-resolution volume data set from a portion of the projections which correspond to a selected cardiac phase;
    Estimating a three-dimensional centerline in the volume data;
    Forward projecting at least one of the volume data and the three-dimensional centerline into the projections of the angiography data set;
    Using the forward projected volumes or the centerlines as initial approximations for correct motion-compensation of the projection at each viewing angle;
    Calculating a transformation matrix between the initial approximation and the projection at each viewing angle;
    Transforming the projection at each viewing angle with the corresponding transform matrix to transform the projection into the selected cardiac phase;
    Reconstructing the transformed projections into a three-dimensional projection image.

17. An X-Ray apparatus comprising:

an X-Ray facility for forming a set of a plurality of two-dimensional X-Ray projection images of an object to be examined through a scanning rotation by an X-Ray source, which X-Ray projection images are acquired as the object undergoes substantially periodic motion, and which X-ray projection images each have one of a plurality of projection orientations;

a data processor which reconstructs by back-projection a selected phase three-dimensional volume image of said object from a subset of X-Ray projection images which were acquired in a selected phase of the periodic motion, forward projects the selected phase three-dimensional volume image into each of the projection orientations, derives a motion correction for each of the projection orientations based on the acquired projection image and the forward projection image corresponding to each projection orientations, corrects the acquired projection images with the corresponding derived motion correction, and reconstructs the motion corrected acquired images into a motion corrected three-dimensional volume image.

* * * * *